United States Patent [19]
Scadden et al.

[11] Patent Number: 6,004,812
[45] Date of Patent: Dec. 21, 1999

[54] IN-VITRO T-LYMPHOPOIESIS SYSTEM

[75] Inventors: David T. Scadden, Weston, Mass.; Andrew Freedman, Wales, United Kingdom

[73] Assignee: Beth Israel Medical Center, Inc., Boston, Mass.

[21] Appl. No.: 09/132,206

[22] Filed: Aug. 11, 1998

Related U.S. Application Data

[60] Division of application No. 08/475,679, Jun. 7, 1995, which is a continuation-in-part of application No. 08/348,659, Dec. 1, 1994.

[51] Int. Cl.$^6$ ........................................................ C12N 5/08
[52] U.S. Cl. ...................... 435/372.3; 435/347; 435/372; 435/373; 435/377; 435/386
[58] Field of Search ..................................... 435/347, 325, 435/326, 363, 366, 372, 372.3, 373, 377, 384, 386, 387

[56] References Cited

U.S. PATENT DOCUMENTS

| | | | |
|---|---|---|---|
| 5,061,620 | 10/1991 | Tsukamoto et al. | 435/7.21 |
| 5,236,706 | 8/1993 | Debre et al. | 424/85.2 |

FOREIGN PATENT DOCUMENTS

| | | |
|---|---|---|
| 0 479 280 A1 | 4/1992 | European Pat. Off. . |
| WO 90/10059 | 7/1990 | WIPO . |
| WO 93/12805 | 8/1993 | WIPO . |
| WO 94/04658 | 3/1994 | WIPO . |

OTHER PUBLICATIONS

Lyman et al. Cell, vol. 75, pp. 1157–1167, 1993.
Jacobsen et al. J. Exp. Med., vol. 178, pp. 413–418, 1993.
Jacobsen et al. J. Exp. Med., vol. 181, pp. 1357–1363, 1995.
Benveniste et al., "Development of T Cells In Vitro from Precursors in Mouse Bone Marrow", Cellular Immunology, 127, 92–104, 1990.
Boyle et al., "Adoptive Transfer of Cytotoxic T Lymphocytes for the Treatment of Transplant–Associated Lymphoma", Surgery, vol. 114, No. 2, pp. 218–225, Aug. 1993.
Chervenak et al., "Characterization of the Progeny of Pre–T Cells Maintained In Vivo by IL–3: Expression of the IL–2 Receptor and CD3 During Thymic Development", Cellular Immunology, 134, 349–358, 1991.
DiGiusto et al., "Human Fetal Bone Marrow Early Progenitors for T, B, and Myeloid Cells are Found Exclusively in the Population Expressing High Levels of CD34", Blood, vol. 84, No. 2, pp. 421–432, Jul. 15, 1994.
Hurwitz, "A Programmed Functional and Phenotypic Development of Bone Marrow–Derived Cytotoxic Cell Precursors In Vitro", J. Immunol, 17, pp. 751–756, 1987.
Soloff et al., "Characterization of the Progeny of Pre–T Cells Maintained In Vitro by IL–3: Appearance in the Periphery and Vβ Utilization In Vitro", Cellular Immunology, 135, pp. 132–142, 1991.
Tjonnfjord et al., "T Lymphocyte Differentiation In Vitro Adult Human Prethymic CD34$^+$ Bone Marrow Cells", J. Exp. Med., vol. 177, pp. 1531–1539, Jun. 1993.
Toki et al., "Analyses of T–Cell Differentiation from Hemopoietic Stem Cells in the $G_0$ Phase by an In Vitro Method", Proc. Natl. Acad. Sci., vol. 88, pp. 7548–7551, Sep. 1991.
Berenson et al. (1988) "Antigen CD34+ Marrow Cells Engraft Lethally Irradiated Baboons" *J. Clin. Invest.* 81:951–955.
Berenson et al. (1991) "Engraftment After Infusion of CD34+ Marrow Cells in Patients With Breast Cancer or Neuroblastoma" *Blood* 77:1717–1722.
Exine et al. (1984) "Bone marrow cells give rise to distinct cell clones within the thymus" *Nature* 309:629–632.
Gao et al. (1993) "Low Levels of Deoxynucleotides in Peripheral Blood Lymphocytes: A Strategy to Inhibit Human Immunodeficiency Virus Type 1 Replication" *Proc. Natl. Acad. Sci. USA* 90:8925–8928.
Goldschneider et al. (1986) "Studies of Thymocytopoiesis in Rats and Mice I. Kinetics of Appearance of Thymocytes Using a Direct Intrathymic Adoptive Transfer Assay for Thymocyte Precursors" *J. Exp. Med.* 163:1–17.
Huang et al. (1990) "The Hematopoietic Growth Factor KL Is Encoded by the SI Locus and Is the Ligand of the c–kit Receptor, the Gene Product of the W Locus" *Cell* 63:225–233.
Jansen et al. (1982) "Immunotoxins: Hybrid Molecules Combining High Specificity and Potent Cytotoxicity" *Immunol. Rev.* 62:185–216.
Killen et al. (1984) "Specific Killing of Lymphocytes That Cause Experimental Autoimmune Myasthenia Gravis By Ricin Toxin–Acetylcholine Receptor Conjugates" *J. Immun.* 133:2549–2553.
McCune et al. (1988) "The SCID–hu Mouse: Murine Model for the Analysis of Human Hematolymphoid Differentiation and Function" *Science* 241:1632–1639.
Meyerhans et al. (1994) "Restriction and Enhancement of Human Immunodeficiency Virus Type 1 Replication by Modulation of Intracellular Deoxynucleoside Triphosphate Pools" *J. Virol.* 68:535–540.
Namikawa et al. (1990) "Long–Term Human Hematopoiesis in the SCID–hu Mouse" *J. Exp. Med.* 172:1055–1063.
Peault et al. (1991) "Lymphoid Reconstitution of the Human Fetal Thymus in SCID Mice with CD34+ Precursor Cells" *J. Exp. Med.* 174:1283–1286.

(List continued on next page.)

*Primary Examiner*—Jon P. Weber
*Assistant Examiner*—Janet M. Kerr
*Attorney, Agent, or Firm*—Lahive & Cockfield, LLP; Ralph A. Loren, Esq.

[57] ABSTRACT

The present invention provides an in vitro T-lymphopoiesis system in which a population of T-cells is produced from precursor cells expressing CD34. The T-lymphopoiesis system of the present invention produces a population of T-cells of which approximately 17–74% express CD2, approximately 1.5–34% express CD3, and approximately 16–61% express CD4, and approximately 0–15% express CD8. A method of producing such a population of T-cells in vitro, as well as various compositions including T-cells of the present invention, are also provided.

4 Claims, 8 Drawing Sheets

OTHER PUBLICATIONS

Soloff et al. (1991) "Characterization of the Progeny of Pre–T Cells Maintained In Vitro by IL–3; Appearance in the Periphery and Vβ Utilization In Vitro" *Cellular Immunology* 135:132–142.

Terstappen et al. (1992) "Flow Cytometric Assessment of Human T–Cell Differentiation in Thymus and Bone Marrow" *Blood* 79:666–677.

Tsubota et al. (1990) "CD4–Pseudomonas Exotoxin Conjugates Delay but Do Not Fully Inhibit Human Immunodeficiency Virus Replication in Lymphocytes in Vitro" *J. Clin. Invest.* 86:1684–1689.

Williams et al. (1988) "Generation of Murine Stromal Cell Lines Supporting Hematopoietic Stem Cell Proliferation by Use of Recombinant Retrovirus Vectors Encoding Simian Virus 40 Large T Antigen" *Mol. Cell Biol.* 8:3864–3871.

Zsebo et al. (1990) "Identification, Purification, and Biological Characterization of Hematopoietic Stem Cell Factor from Buffalo Rat Liver—Conditioned Medium" *Cell* 63:195–201.

Cesano, A., et al., "Cellular and Molecular Mechanisms of Activation of MHC Nonrestricted Cytotoxic Cells by IL–12," *The Journal of Immunology*, vol. 151, No. 6, 2943–2957 (1993).

Clerici, M., et al., "Restoration of HIV–Specific Cell–Mediated Immune Responses by Interleukin–12 in Vitro," *Science*, vol. 262, 1721–1724 (1993).

Gately, M., et al., "Regulation of Human Lymphocyte Proliferation by a Heterodimeric Cytokine, IL–12 (Cytotoxic Lymphocyte Maturation Factor)," *The Journal of Immunology*, vol. 147, No. 3, 874–882 (1991).

Perussia, B., et al., "Natural Killer (NK) Cell Stimulatory Factor or IL–12 has Differential Effects on the Proliferation of TCR–αβ$^+$, TCR–γδ$^+$T Lymphocytes, and NK Cells," *The Journal of Immunology*, vol. 149, No. 11, 3495–3502 (1992).

IN-VITRO T-LYMPHOPOIESIS SYSTEM

This application is a divisional application of Ser. No. 08/475,679 filed on Jun. 7, 1995, Pending, which in turn is a continuation-in-part application of Ser. No. 08/348,659 filed on Dec. 1, 1994, pending. The contents of all of the aforementioned applications are hereby incorporated by reference.

GOVERNMENT SUPPORT

The work described herein was supported, in part, by a grant from the National Institutes of Health (HL 44851). The United States government may have certain rights in the invention.

BACKGROUND OF THE INVENTION

T-lymphocytes, or T-cells, are cornerstones of the mammalian immune system, responsible for cell-mediated immunity against foreign antigens. T-cells, like other lymphocytes, develop from pluripotent hematopoietic stem cells produced primarily in hematopoietic tissues (i.e. in the liver in fetuses and in bone marrow in adults). Some of these precursor stem cells migrate through the blood to the thymus, and T-cell differentiation occurs there.

The majority of T-lymphocytes are immune system regulators, known as helper T cells and suppressor T cells, that act either to enhance or suppress the immune responses of other white blood cells. Other T-lymphocytes, called cytotoxic T-cells, act to kill virus-infected cells. These different types of T-cells are distinguished from one another by the presence of different antigenic markers on their surfaces. Specifically, helper T-cells express a cell-surface glycoprotein known as CD4, and cytotoxic T-cells express a different cell-surface glycoprotein, CD8. As T-cells mature, they express the CD2 cell-surface protein, and, ultimately, the CD3 cell-surface protein complex.

T-cell development has been intensively studied in vivo. The evidence indicates that pluripotent hematopoietic stem cells are present in populations of cells expressing CD34 surface molecules (CD34$^+$ cells; see, for example, Terstappen et al. Blood, 79:666–677, 1992 and references cited therein). Such CD34$^+$ cells represent about 1% of nucleated bone marrow cells. CD34$^+$ cells have been used to successfully repopulate the thymus of an irradiated host with T-cells (see, for example, Exine et al. Nature 309:629–632, 1984; Goldschneider et al. J. Exp. Med. 163:1–17, 1986; Berenson et al. J. Clin. Invest. 81:951–955, 1988); and engraftment of human CD34+ progenitor cells into mice with genetically determined severe combined immunodeficiency (SCID mice) has been observed to result in development of mature T-lymphocytes in those mice (see, for example, McCune et al. Science 241:1632–1639, 1988; Namikawa et al. J. Exp. Med. 172:1055–1063, 1990; Berenson et al. Blood 77:1717–1722, 1991).

Efforts have also been directed at developing an in vitro T-lymphopoiesis system (see, for example, Benveniste et al. Cell. Immunol. 127:92–104; Peault et al. J. Exp. Med. 174:1283–1286, 1991; Toki et al. Proc. natl. Acad. Sci. USA 88:7548–7551, 1991; Tjonnfjord et al. J. Exp. Med. 177:1531–1539; Hurwitz, J. Immunol. 17:751–756, 1987). Peault et al. have developed a system in which CD34+ cells from human fetal liver and bone marrow are microinjected in vitro into HLA-mismatched fetal thymus fragments previously depleted of hematopoietic stem cells by low temperature culture. Peault et al. have not achieved complete in vitro T-cell development, however, as the in vitro-colonized thymuses were subsequently engrafted into SCID mice, and T-cell differentiation occurred in vivo.

Tjonnfjord et al. have reported in vitro T-cell differentiation from adult human CD34+ bone marrow cells cultured in thymic stromal cell supernatant and in the presence or absence of recombinant murine c-kit ligand. Nevertheless, Tjonnfjord et al. found that only a small fraction of their total cell culture (see FIG. 3 of Tjonnfjord et al.) developed into mature T-cells, as indicated by the presence of T-cell-specific surface markers such as CD2, CD3, CD4, and CD8. Thus, there remains a need for the development of an in vitro T-lymphopoiesis system in which a significant fraction of the cultured cells develop into mature T-cells.

SUMMARY OF THE INVENTION

The present invention provides an in vitro T-lymphopoiesis system in which a significant fraction of the cultured cells develop into mature T-cells. Approximately 17–74% of the cells produced in the in vitro T-lymphopoiesis system of the present invention express the T-cell-specific surface antigen CD2; 1.5–34% express CD3; 16–61% express CD4 and 0–15% express CD8. No expression of CD15 or CD56 (natural killer cell phenotype) was detected.

The present invention therefore provides an isolated population of T-cells produced in vitro from precursor cells expressing CD34, in which approximately 17–74% of the T-cells in the population express CD2, approximately 1.5–34% of the T-cells in the population express CD3, and approximately 16–61% of the T-cells in the population express CD4. The population of T-cells of the present invention expresses the lymphocyte-specific RAG-2 gene. Furthermore, T-cells produced in the present in vitro system are sensitive to infection by the T-cell-tropic human immunodeficiency. virus (HIV) strain HIV-1$_{IIIB}$. The T-cells of the present invention can therefore be utilized to identify drugs that affect HIV infection of developing T-cells.

The present invention also provides a method of producing T-cells in vitro comprising the steps of i) providing a population of precursor cells expressing CD34; and ii) culturing the precursor cells in the presence of interleukin-12 (IL-12). Preferably, the precursor cells are human bone marrow cells, human umbilical cord blood cells, human peripheral blood cells, or human fetal liver cells. The precursor cells can be cultured in the presence of a confluent monolayer of thymic stroma and a cytokine or combination of cytokines including IL-12, preferably in combination with flk2/flt3 ligand. In most preferred embodiments of the method of the present invention, IL-12 is present at a concentration of about 10 ng/ml, and flk2/flt3 ligand is present at a concentration of about 100 ng/ml.

The in vitro-produced T-cells of the present invention can be used in pharmaceutical compositions, at therapeutically effective amounts. Preferably, such compositions include a pharmaceutically-acceptable carrier and/or a pharmaceutically-acceptable salt.

The in vitro-produced T-cells of the present invention can also be used to identify drugs or factors that affect T-cell development. The invention also provides a combination including i) a population of CD34 positive mammalian bone marrow cells that is at least about 95 percent pure; and ii) interleukin-12, and preferably also including iii) flk2/flt3 ligand; iv) a population of thymic stromal cells; and/or v) a drug.

DESCRIPTION OF THE PREFERRED EMBODIMENTS

As indicated above, the present invention provides an effective in vitro T-lymphopoiesis system. Essentially, CD34+ cells are plated onto a confluent monolayer of "feeder" cells, and are cultured in the presence of selected growth factors to induce T-cell differentiation. The preferred tissue source for preparation of the feeder cell layer is human fetal thymic tissue, although other sources, such as, for example, thymic stroma from non-human primates or other mammals, or immortalized cell lines derived from the above-mentioned sources may alternately be utilized. The feeder layer can be prepared using standard techniques known in the art (see, for example, Tjonnfjord et al. supra). The preferred method of preparation of the feeder layer is described below in Example 1.

CD34+ cells for use in the present invention can be obtained from a variety of different sources such as, for example, bone marrow, umbilical cord blood, peripheral blood stem, and fetal liver. The preferred source of CD34+ cells, due in part to its ready availability, is bone marrow. CD34+ cells utilized in the present invention can be purified using any available method such as, for example, fluorescence-activated cell sorter SACS) analysis, immuno-magnetic bead purification (or other immunoprecipitation method), or functional selection using cytokines in conjunction with anti-metabolites, and should be at least approximately 95% pure (i.e. at least approximately 95% of the cells should express CD34).

Figure 1:
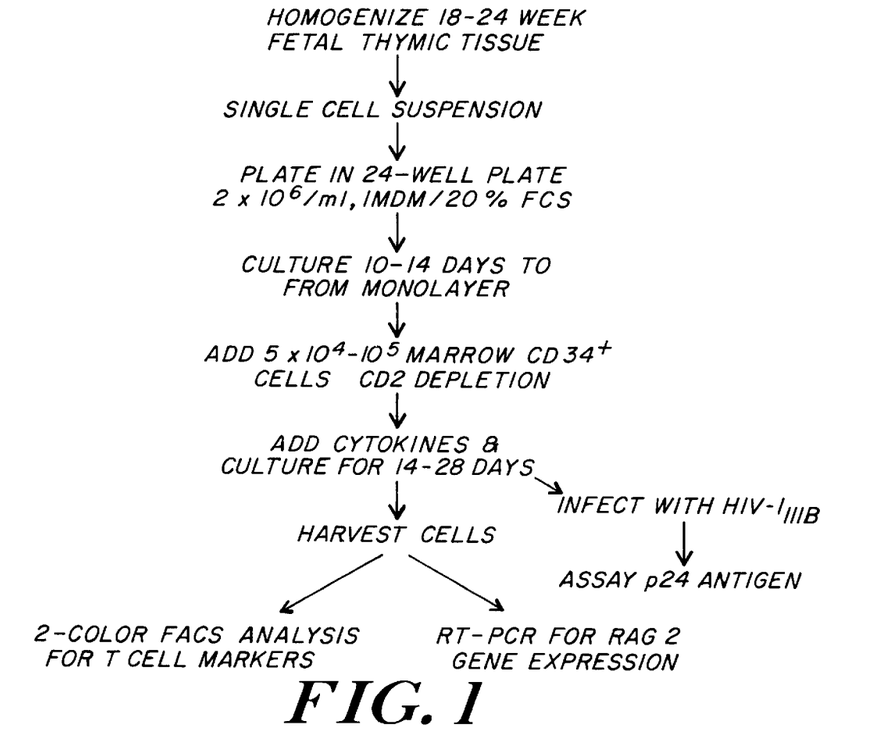
FIG. 1 shows a schematic of a preferred embodiment of the method of the present invention.
Figure 2:
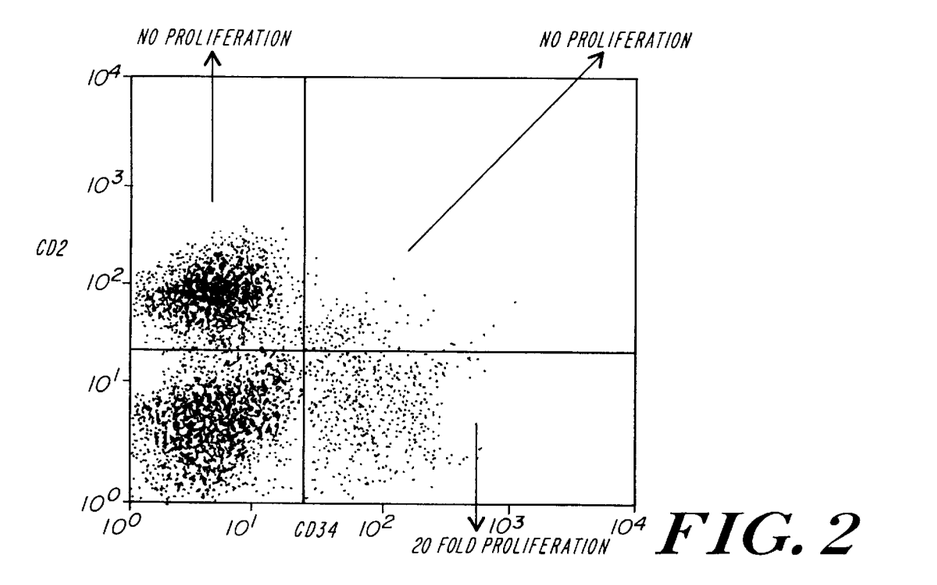
FIG. 2 illustrates the proliferative capabilities of various immunophenotypic subtypes of low density bone marrow mononuclear cells used as precursors in a preferred embodiment of the in vitro T-lymphopoiesis system of present invention.

The purified CD34+ cells are plated on the feeder layer and cultured in the presence of a cytokine or mixture of cytokines, preferably including interleukin-12 (IL-12) and possibly also including flk2/flt3 ligand, for at least approximately two weeks, and typically less than or equal to approximately 35 days. Not all cytokine preparations are equally effective in the in vitro T-lymphopoiesis system of the present invention. In particular, we have found that IL-2, IL-7, and SCF are not as effective as is IL-12 in stimulating development of a significant fraction of cells into mature T-cells. Typically, cells proliferate in the in vitro system of the present invention approximately 20–25 fold in fourteen days of culture (see FIG. 2).

After the culture period, cells produced in the in vitro system of the present invention can be analyzed for expression of T-cell markers and/or for T-cell activity using any available method including, for example, FACS analysis to detect T-cell surface markers such as, for example, CD2, CD3, CD4, CD7, CD8, CD25, and CD44. Typically, approximately 17–74% of the cells produced in the in vitro T-lymphopoiesis system of the present invention express detectable CD2, approximately 1.5–34% express detectable CD3, and approximately 16–61% express detectable CD4. Cell cultures produced by this in vitro system have fewer cells expressing CD8; that is, fewer than or equal to approximately 15% of the cells produced in the present in vitro system are CD8+.

Figure 4:
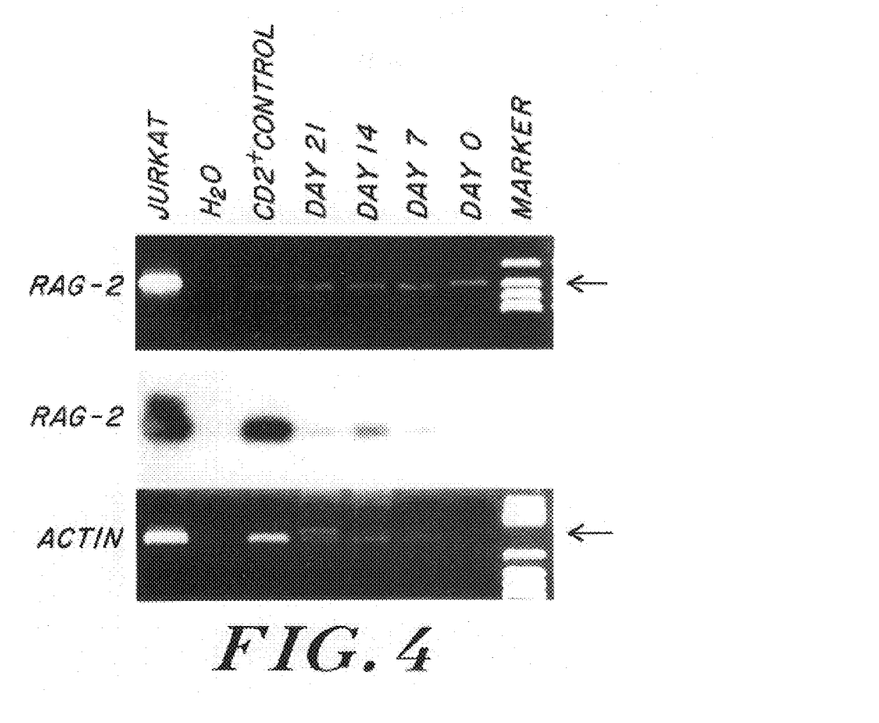
FIG. 4 presents PCR and Southern blot results demonstrating that CD34+ cells acquire RAG-2 expression during culture in the in vitro T-lymphopoiesis system of the present invention.
Figure 7:
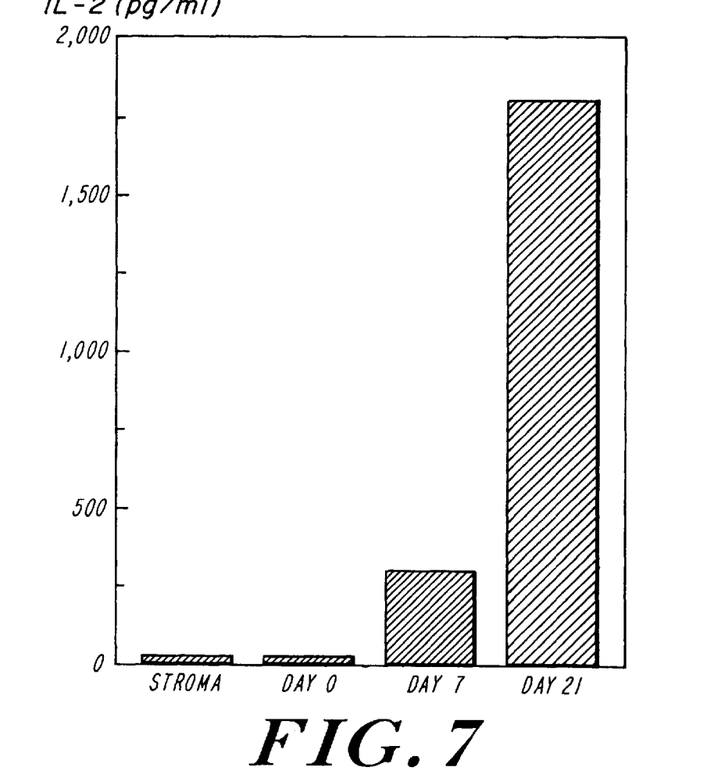
FIG. 7 is a bar graph showing detection of IL-2 by ELISA in cultured cells of the present invention.
Figure 8A:
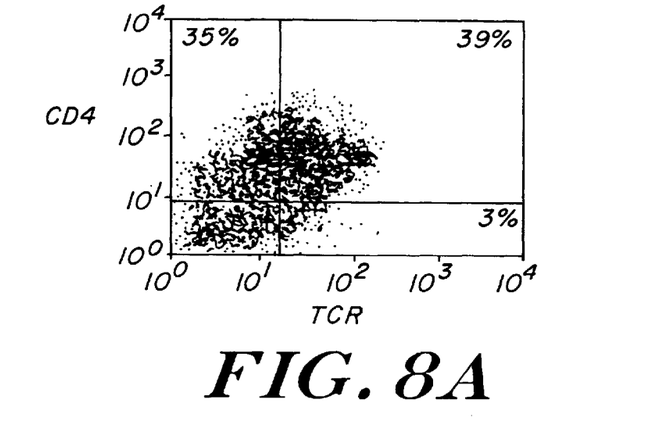
FIG. 8 illustrates the acquisition of TCR expression by cultured cells. Day 21 cells were stained with anti-CD4-PE and anti-TCRα/β-1-FITC prior to flow cytometric analysis (A). RNA derived from day 21 trypsinized thymic stroma alone, cultured CD34+ cells or control CD2+ cells was analyzed by RT PCT for TCR expression.
Figure 8B:
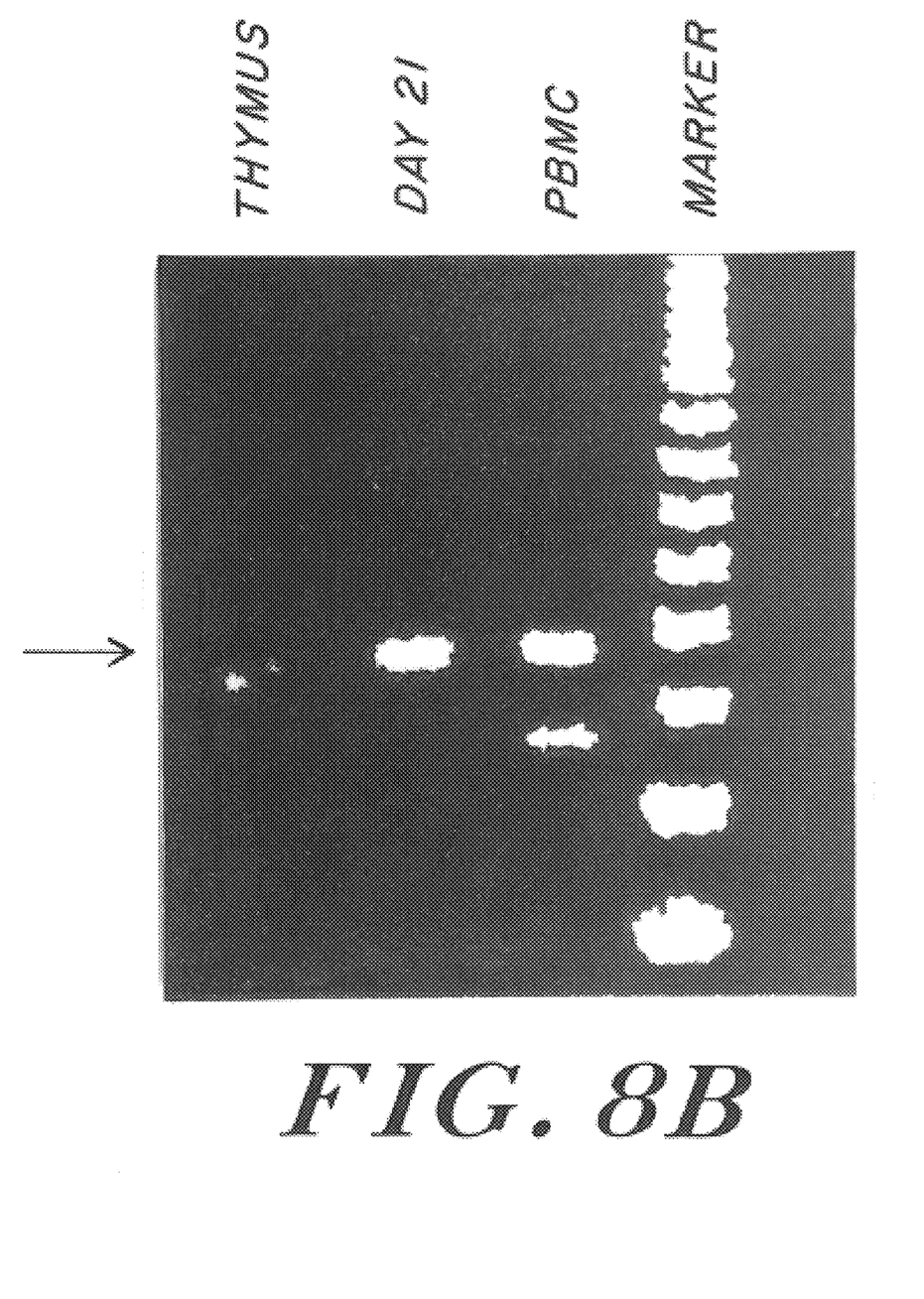

Cultured cells of the present invention can also be analyzed for expression of T-cell-specific genes (such as, for example, RAG-2 or T-cell receptor (TCR) genes) and/or for production of T-cell specific proteins (e.g. IL-2) using known techniques of molecular biology (see, for Example, Sambrook et al. *Molecular Cloning: A Laboratory Manual* Cold Spring Harbor Press, New York, 1989, incorporated herein by reference). Acquisition of RAG-2 expression is detectable during the culture period (see FIG. 4). In addition, acquisition of TCRβ expression is detectable during the culture period (see FIG. 8). IL-2 production is detectable in cultured cells produced in the in vitro T-lymphopoiesis system of the present invention (see FIG. 7). Detection of IL-2 confirms that the cultured cells are mature T-cells.

T-cells produced in the in vitro system of the present invention can be tested for proliferative responses to mitogens such as PHA, PMA, anti-CD3 receptor (with IL-2), or for proliferative response to antigens, using known techniques.

Figure 5:
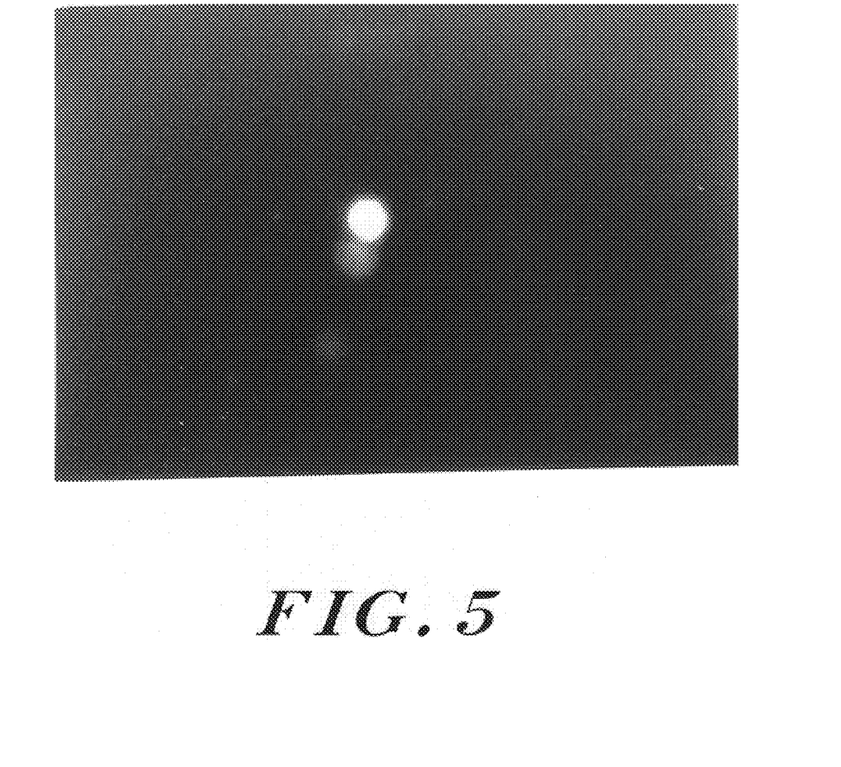
FIG. 5 is a fluorescence photomicrograph showing T-cells of the present invention stained with HIV antiserum and anti-human FITC, 14 days after exposure to HIV-1$_{IIIB}$.
Figure 6A:
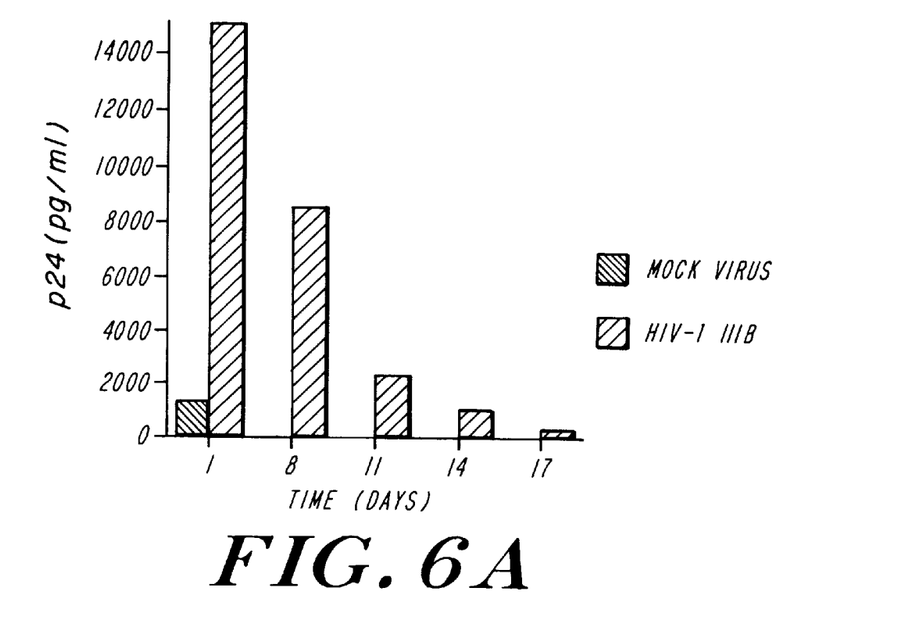
FIG. 6 presents two graphs showing supernatant HIV p24 antigen levels from parallel cultures of stroma alone (panel A) and stroma with CD34+ cells (panel B) after exposure to HIV-1$_{IIIB}$ or heat-inactivated (mock) virus. The increase in p24 after 11 days in the cultures containing CD34+ cells, but not thymic stroma alone, is evidence of productive HIV infection of developing T-cells.
Figure 6B:
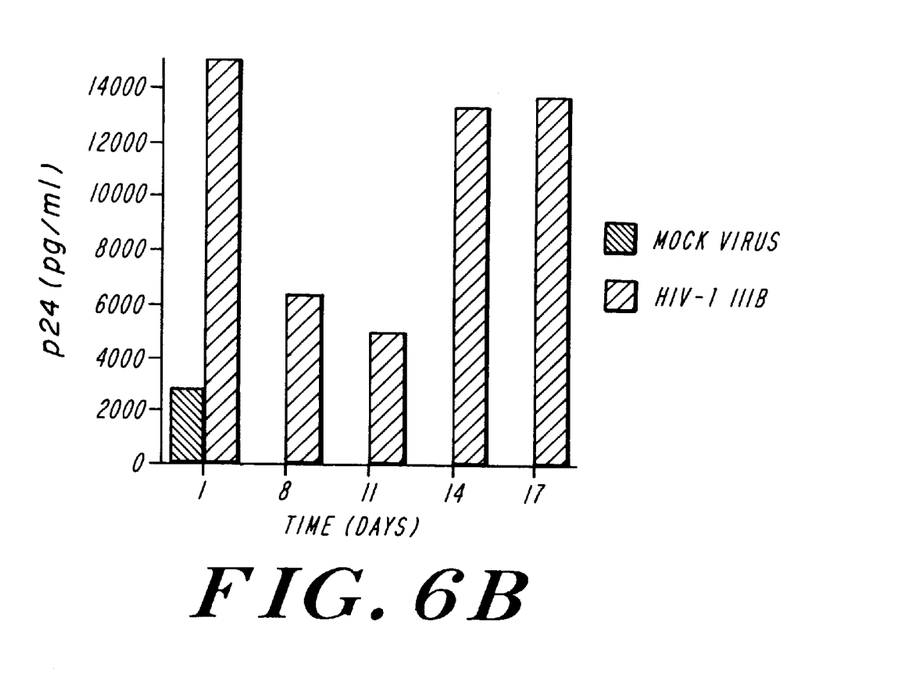

Cultured cells of the present invention are susceptible to infection by lymphotrophic pathogens. In particular, cultures cells are susceptible to infection with a T-cell-tropic strain of the human immunodeficiency virus, HIV-1$_{IIIB}$. For example, after 14 days of culture on a thymic stroma feeder layer, T-cells of the present invention that have been exposed to HIV-1$_{IIIB}$ produce the HIV p24 antigen, that is detectable in the cell supernatant (see FIG. 6). Cultured cells that are exposed to mock virus preparations, or to heat-inactivated virus, do not produce detectable p24. HIV-1$_{IIIB}$-exposed cells also stain positively for HIV using HIV-1 antisera (see FIG. 5).

The present invention therefore provides an effective in vitro T-lymphopoiesis system. The in vitro system of the present invention can be utilized to study T-cell development, and also to identify potential drug candidates that interfere with or enhance a given step in differentiation and/or proliferation of T-cells. For example, drugs can be added to the culture system of the present invention, and the effect of those drugs on number, immunophenotype, reactivity to known T-cell stimuli (such as, for example, PHA, PMA, anti-CD3 receptor plus IL-2), or infection by specific pathogens (such as, for example, HIV or HTLV) of the product T-cells can be determined by comparison with cultures to which no drugs have been added, or to which a "placebo" has been added. A "placebo" is a compound that does not significantly affect the parameter (e.g. cell number, etc.) being measured. The specific nature of the "placebo" used in a given test depends on the character of the drug to which it is being compared. For example, if the drug in question is a protein, an appropriate placebo would be a denatured version of that protein. One of ordinary skill in the art could readily identify appropriate placebos for comparison with given drugs.

Exemplary drugs that can be tested in the in vitro T-lymphopoiesis system of the present invention include any and all compounds suspected of having an effect on T-cell development and/or proliferation, e.g., cyclophilins. In fact, the in vitro T-lymphopoiesis system of the present invention can also be utilized as a source of compounds to be tested. That is, the present in vitro T-lymphopoiesis system, or components thereof, can be fractionated according to known procedures (see, for example, Huang et al. Cell 63:225–233, 1990; Zsebo et al. Cell 63:195–201, 1990, each of which is incorporated herein by reference), and individual fractions can be tested for their effects on T-cell development. Fractions having desirable activities (e.g. fractions that affect one or more aspects of T-cell development and/or proliferation) can be further fractionated according to known techniques, until individual active factors are identified. Active factors can subsequently be purified, and genes encoding protein factors can be cloned, according to techniques available in the art, such as those disclosed in *Current Protocols in Molecular Biology* (John Wiley & Sons) and *Current Protocols in Immunolgy* (John Wiley & Sons).

Active factors that affect T-cell development and/or proliferation can, for example, be derived from stromal components of the in vitro T-lymphopoiesis system of the present invention. Either non-immortalized or immortalized primary stromal cells can be utilized. Immortalization techniques (such as, for example, transduction with Simian Virus 40 (SV40) large T-antigen or middle T-antigen are known in the art (see, for example, Williams et al. Mol. Cell. Biol. 8:3864, 1988).

The culture system of the present invention has the additional advantage that drugs can be added at different times, so that the point during T-cell ontogeny that a given drug (or combination of drugs) exerts it's effects can readily be determined.

Another valuable application for the present in vitro T-lymphopoiesis system and cells produced thereby is as a system for genetic manipulation of T-cells. Foreign genetic material can be introduced into, for example, the CD34$^+$ precursor cells prior to culturing in the presence of a cytokine, using any available method of gene transfer such as, for example, transformation, transfection, infection (using, for example, retroviral vectors or adeno- or adeno-associated viruses), transduction, electroporation, etc. (see, for example, Sambrook et al. supra).

T-cells containing genes, such as, for example, dominant negative HIV-1 rev mutants or HIV-1 antisense constructs, that protect T-cells from infection can be produced using the in vitro system of the present invention. Other genes that can desirably be introduced into T-cells using the in vitro T-lymphopoiesis system of the present invention include, for example, genes encoding antibodies of known specificity; receptor ligand gene constructs, genes that enhance T-cell reactivity (such as genes encoding cytokines, cytokine receptors, or "co-stimulatory molecules such as, for example, CD28, B7, CD40, CD40 ligand, etc.). In some instances, it may be desirable to introduce genes that limit T-cell reactivity, so that the product T-cells of the present invention will have increased tolerance relative to T-cells that have not been subjected to similar genetic manipulation.

Additionally, the present in vitro T-lymphopoiesis system may be utilized to produce T-cells with specific reactivity. An antigen, such as a peptide, can be added to the culture system in order to induce proliferation of a subset of T-cells reactive against that antigen. In some cases, as will be apparent to one of ordinary skill in the art, it is desirable that the antigen be presented in the context of an antigen-presenting cell such as, for example, a T2 cell, an activated B cell, a macrophage, or a dendritic cell. Such reactive T-cells of the present invention could be utilized, for example, in adoptive immunotherapy applications in order to generate a targeted immunologic reaction for the treatment of disorders such as, for example, malignancies or infectious diseases.

In fact, T-cells produced in the in vitro system of the present invention, whether or not they have a specific reactivity, can be utilized in a variety of therapeutic techniques. In particular, the T-cells produced in the system of the present invention can be used in pharmaceutical compositions in, for example, adoptive immunotherapy, vaccine therapy and/or gene therapy. An exemplary pharmaceutical composition including a T-cell of the present invention is a therapeutically effective amount of the T-cell, which may or may not have been transfected (or transformed or infected, etc.) with a gene sequence capable of expressing a particular gene product (see above), optionally combined with a pharmaceutically-acceptable and compatible carrier. The term "pharmaceutically-acceptable and compatible carrier" as used herein, and described more fully below, refers to (i) one or more compatible filler diluents or encapsulating substances that are suitable for administration to a human or other animal, and/or (ii) a system capable of delivering the T-cell to a target. In the present invention, the term "carrier" thus denotes an organic or inorganic ingredient, natural or synthetic, with which the T-cells of the invention can be combined to facilitate administration.

The term "therapeutically-effective amount" refers to that amount of the present pharmaceutical compositions which produces a desired result or exerts a desired influence on the particular condition being treated. Various concentrations may be used in preparing compositions incorporating the same ingredient to provide for variations in the age of the patient to be treated, the severity of the condition, the duration of the treatment and/or the mode of administration.

The term "compatible", as used herein, means that the components of the pharmaceutical compositions are capable of being co-mingled with the T-cells of the present invention, and with each other, in a manner such that there is no interaction that would substantially impair the desired pharmaceutical efficacy.

T-cells of the present invention may be administered per se (neat) or in combination with a pharmaceutically acceptable salt. Non-pharmaceutically acceptable salts may, in some instances, conveniently be used to prepare pharmaceutically acceptable salts, and are therefore not excluded from the scope of this invention. Pharmaceutically acceptable salts include, but are not limited to, those prepared from the following acids: hydrochloric, hydrobromic, sulphuric, nitric, phosphoric, maleic, acetic, salicylic, p-toluenesulfonic, tartaric, citric, methanesulphonic, formic, malonic, succinic, naphthalene-2-sulfonic, and benzenesulphonic. Also, pharmaceutically acceptable salts can be prepared as alkaline metal or alkaline earth salts, such as sodium, potassium or calcium salts of the carboxylic acid group.

The pharmaceutical compositions of the present invention are most suited for parenteral administration. The term "parenteral" includes subcutaneous injections, intravenous, intramuscular, intrasternal injection or infusion techniques. Preferred compositions suitable for parenteral administration may comprise a sterile aqueous preparation of the T-cells of the invention which is preferably isotonic with the blood of the recipient. Among the acceptable vehicles and solvents that may be employed are water, Ringer's solution and isotonic sodium chloride solution.

The T-cells of the invention can also be conjugated to a moiety for use in, for example, vaccines. The moiety to which the T-cells are conjugated can be a protein, carbohydrate, lipid, and the like. Coupling may be accomplished by any chemical reaction that will bind the T-cell and another molecule so long as the two moieties retain their respective activities. This linkage can include many chemical mechanisms, for instance covalent binding, affinity binding, intercalation, coordinate binding and complexation. The preferred binding is covalent binding. Covalent binding can be achieved either by direct condensation of existing side chains or by the incorporation of external bridging molecules. Many bivalent or polyvalent linking agents are useful in coupling, for example, protein molecules to other molecules (e.g. molecules associated with the T-cells of the present invention).

For example, representative coupling agents can include organic compounds such as thioesters, carbodiimides, succinimide esters, diisocyanates, glutaraldehydes, diazobenzenes and hexamethylene diamines. This listing is not intended to be exhaustive of the various classes of coupling agents known in the art but, rather, is exemplary of the more common coupling agents (see, for example, Killen et al. J. Immun. 133:1335–2549, 1984; Jansen et al. Immunol. Rev. 62:185–216, 1982; and Vitetta et al., supra).

The moiety to which T-cells may be bound can also be an adjuvant. The term "adjuvant" is intended to include any substance which is incorporated into or administered simultaneously with the T-cells which potentiates an immune response in the subject. Adjuvants include aluminum compounds, e.g., gels, aluminum hydroxide and aluminum phosphate gels, and Freund's complete or incomplete adjuvant. The paraffin oil may be replaced with different types of oils, e.g., squalene or peanut oil. Other materials with adjuvant properties include BCG (attenuated *Mycobacterium tuberculosis* plus other microbial derivatives), calcium phosphate, levamisole, isoprinosine, polyanions (e.g., poly A:U), leutinan, pertussis toxin, lipid A, saponins and peptides, e.g., muramyl dipeptide. Rare earth salts, e.g., of lanthanum and cerium, may also be used as adjuvants. The amount of adjuvant required depends upon the subject and the particular therapeutic used and can be readily determined by one skilled in the art without undue experimentation. An exemplary pharmaceutical composition of the present invention therefore can comprise a therapeutically effective amount of the T-cells of the invention, either alone or in combination with an immunoadjuvant and/or carrier.

Because the cell cultured in the present in vitro system are susceptible to infection by HIV-1, this system can be used to identify drugs that inhibit HIV-1 infection and/or replication, particularly in developing T-cells. The present in vitro system can also be used to identify drugs that inhibit development and/or proliferation of HIV-infected cells. For example, standard virus infection techniques can be employed to infect cells in the in vitro cultures of the present invention with laboratory strains of HIV-1 (such as, for example, HIV-1$_{IIIB}$) or with primary patient isolates from HIV-1-infected individuals. Potential drugs can be added to the cultures at different points during infection and the effects of those drugs on viral infection can be assayed using standard HIV-1 detection systems (such as, for example, assays for HIV-1 p24 antigen, reverse transcriptase assays, immunofluorescence assays, or PCR-based assays) and comparing the results found with infected cultures that are not treated with drugs, or that are treated with a placebo as discussed above. For examples of some potential drugs that could be analyzed using the present system, and of methods for assaying the effects of those drugs on HIV infection, see, for example, Tsubota et al. J. Clin. Invest. 86:1684–1689, 1990; Gao et al. Proc. Natl. Acad. Sci. USA 90:8925–8928, 1993; and Meyerhans et al. J. Virol. 68:535–540, 1994.

EXAMPLES

The following examples provide details of preferred procedures for the in vitro T-lymphopoiesis system of the present invention. These examples are intended to be illustrative of possible procedures that can be utilized in the practice of the present invention, but are not intended to limit the scope thereof.

Example 1

Preparation and Analysis of T-Cells Produced in Vitro

Thymic stromal culture

Thymus glands were removed from electively aborted human fetuses of 18–24 weeks gestation after informed maternal consent (Anatomic Gift Foundation, Laurel, Md.) and transported at room temperature in culture medium. Thymic tissue was minced into small fragments using scalpel blades and then passed through a tissue sieve to obtain a single cell suspension. Cells were washed twice in phosphate buffered saline (PBS) and resuspended in Iscove's modified Dulbecco's medium (IMDM) (Mediatech, Wash., DC) containing 20% FCS (Sigma, St. Louis, Mo.), glutamine, penicillin and streptomycin at a density of $2 \times 10^6$/ml. The cell suspension was plated into 24-well tissue culture plates, 1 ml per well, and cultured for 10–14 days at 37° C. in a humidified incubator containing 5% $CO_2$ to allow a confluent stromal monolayer to form. Thymic cells not used immediately were cryopreserved in 10% DMSO and washed in medium after thawing prior to plating out as above.

$CD34^+$ cell purification from adult bone marrow and fetal liver

Bone marrow samples were obtained with informed consent from healthy adult volunteers by iliac crest aspiration. Fetal livers (18–24 weeks gestation) were obtained as described above for the thymus glands and single cell suspensions were prepared in the same manner. Mononuclear cells (MNC) were separated from the marrow or liver samples by centrifugation over Ficoll-Pacque (Pharmacia Biotechnology, Uppsala, Sweden), washed twice and suspended in IMDM. Bone marrow MNC were cultured overnight to remove adherent cells prior to further purification.

In order to isolate the CD34+ fraction, the cells were first incubated for one hour to 4° C. with mouse anti-human CD34 IgG1 monoclonal antibody (Amac Inc., Westbrook, Me.), washed twice in IMDM and then incubated with Dynabeads M-450 coated with anti-mouse IgG (Dynal Inc., Great Neck, N.Y.) for one hour at 4° C. with gentle agitation. The selected cells were washed four times using a magnet and their purity checked by microscopy. In some experiments, bone marrow MNC were also depleted of cells of T lineage by negative beads selection (via two rounds of negative selection with Dynabeads M-450 coated with mouse anti-CD2 monoclonal IgG1 antibody (Dynal Inc.), or via use of anti-CD34 DETACHABEADS™ (Dynal, Inc.)), or by cell sorting. CD2+CD34− and CD2+CD34+ fractions were purified by FACS for use in control experiments.

Purification of marrow cell fractions by fluorescence-activated cell sorter (FACS) analysis Bone marrow MNC were stained with FITC-conjugated anti-CD34 and PE-conjugated anti-CD2 antibodies, as described below. Stained cells were sorted using a FACS Vantage cell sorter (Becton Dickinson, San Jose, Calif.); two color fluorescence was quantitated with log amplification in the FL1 and FL2 channels and the CD34+ CD2+ and CD34+ CD2− fractions collected separately.

CD34+ cultures

Between $5 \times 10^4$–$10^5$ CD34+ per well, purified as described above, were plated on top of the thymic stromal monolayers which were first washed extensively to remove all non-adherent cells, and, in some experiments, were irradiated with 15 Gy. The cells were then cultured for a further 2–4 weeks in IMDM/20% FCS with and without added cytokines, as described below. Control cultures were performed using either bone marrow stromal monolayers or empty wells with no stroma instead of the thymic stroma. Cultures were fed twice weekly by carefully removing most of the medium from each well and replacing it with 1 ml fresh medium and appropriate cytokines.

Cytokines

The following human cytokines were added in combination to achieve optimal conditions for promoting T lineage differentiation: −5%, Interleukin-12 (IL-12), 10 ng/ml (R&D Systems, Minneapolis, Minn.) and flk2/flt3 ligand, 100/ng (a kind gift from Dr. S. Lyman, Immunex, Seattle, Wash.).

Immunophenotyping of cultured cells by flow cytometry

Cells were harvested from the culture plates at various times between 2–4 weeks after plating by gentle aspiration, so as to leave the stromal cells behind. The cells were counted and their viability assessed by trypan blue staining. Aliquots of between $2$–$5 \times 10^5$ cells were washed twice in PBS and stained with directly conjugated (FITC or PE) mouse monoclonal antibodies to human surface antigens. The antibodies used were as follows: -FITC-anti-CD34 (Amac Inc.), FITC-anti-CD2 and anti-CD7, PE-anti-CD2, anti-CD3, anti-CD4, anti-CD7 and anti-CD8 (Exalpha Corp., Boston, Mass.), FITC-anti-TCRα/β1 (Becton Dickinson), and FITC-anti-CD56+anti-CD16. FITC- and PE-conjugated mouse isotype control antibodies were used for each culture. Staining was performed according to the manufacturer's instructions and cells were fixed in 1% paraformaldehyde prior to analysis by flow cytometry. Flow cytometric analysis was performed on 10,000 cells from each sample using a FACScan cytometer (Becton Dickinson). Dual color immunofluorescence was quantitated using log amplification in the FL1 and FL2 channels and analyzed using LYSYS II (Becton Dickinson) software for the Hewlett Packard 9000 series computer.

Figure 3:
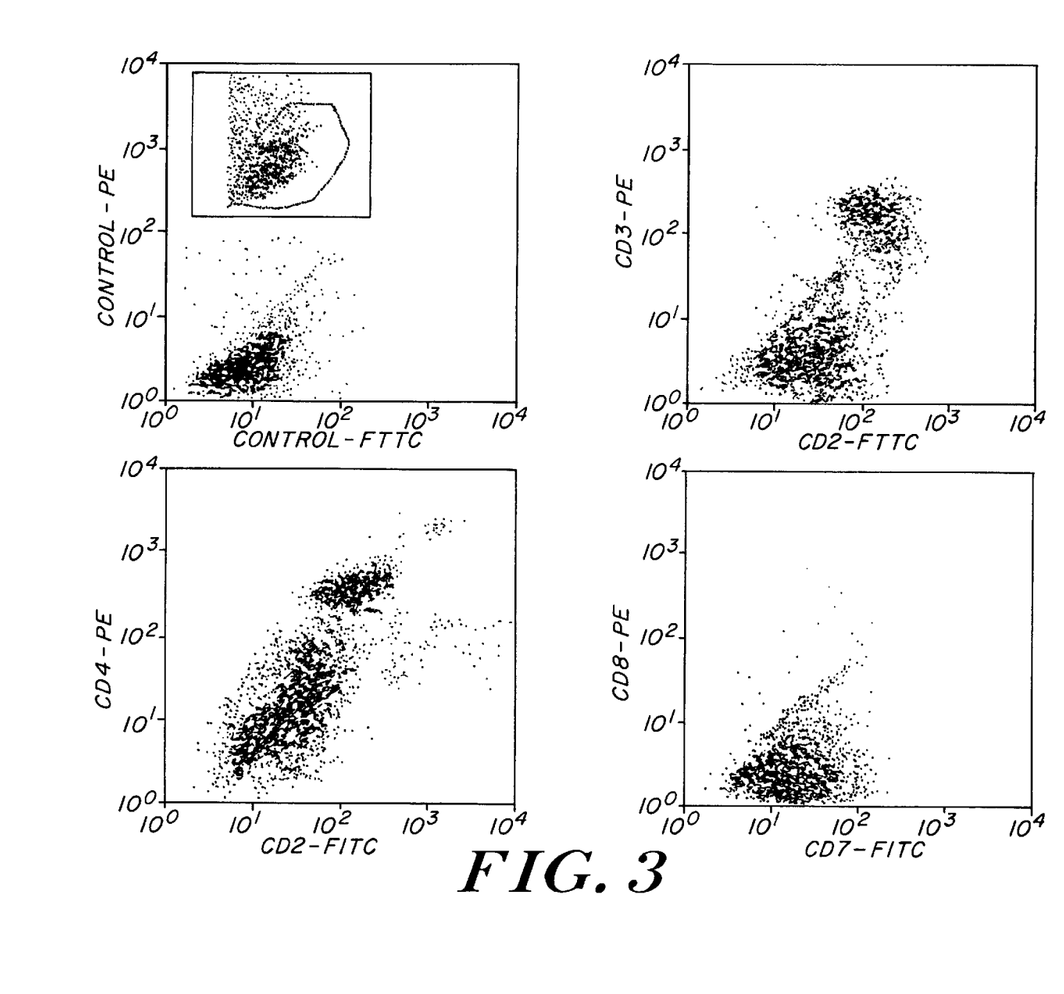
FIG. 3 shows a typical flow cytometric analysis of cells produced in the in vitro T-lymphopoiesis system of the present invention.

FIG. 3 shows a typical flow cytometric analysis of a CD2-depleted, CD34+ cell culture of the present invention that has been supplemented with flk2/flt3 ligand and IL-12, harvested at 21 days. There was considerable variability between cultures, but the combination of flk2/flt3 ligand and IL-12 consistently yielded the highest fraction of cells expressing T cell markers. Culture of purified CD34+ cells for 14–35 days with these cytokines resulted in 17–74% CD2, 1.5–34% CD3 and 16–61% CD4 expression. Expression of CD7 was lower than that of CD2 in most experiments. CD8 expression was low ($\leq 15\%$) in most of the cultures, and there was no detectable expression of CD16 or CD56 (natural killer cell markers).

Figure 9A:
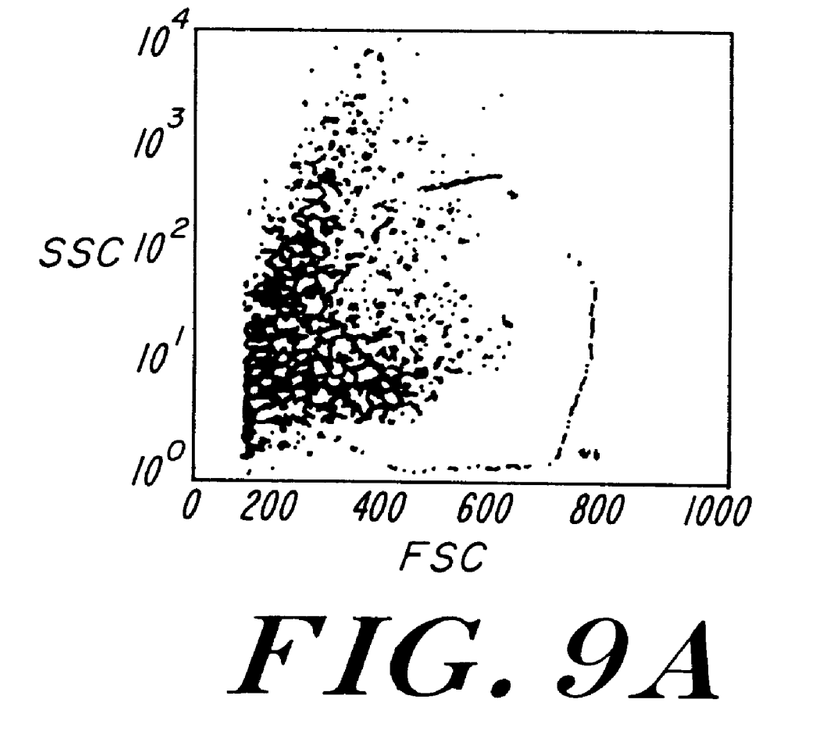
FIG. 9 depicts the immunophenotype of cultivated cells. The output cell population was gated using the forward and side scatter criteria shown (A). The flow cytometric analyses of cells stained with the indicated antibodies at particular time points are shown (B). Each time point required analysis of the entire cell population, therefore, the data shown are from independent cultures and do not represent the sequential sampling of a single culture.
Figure 9B:
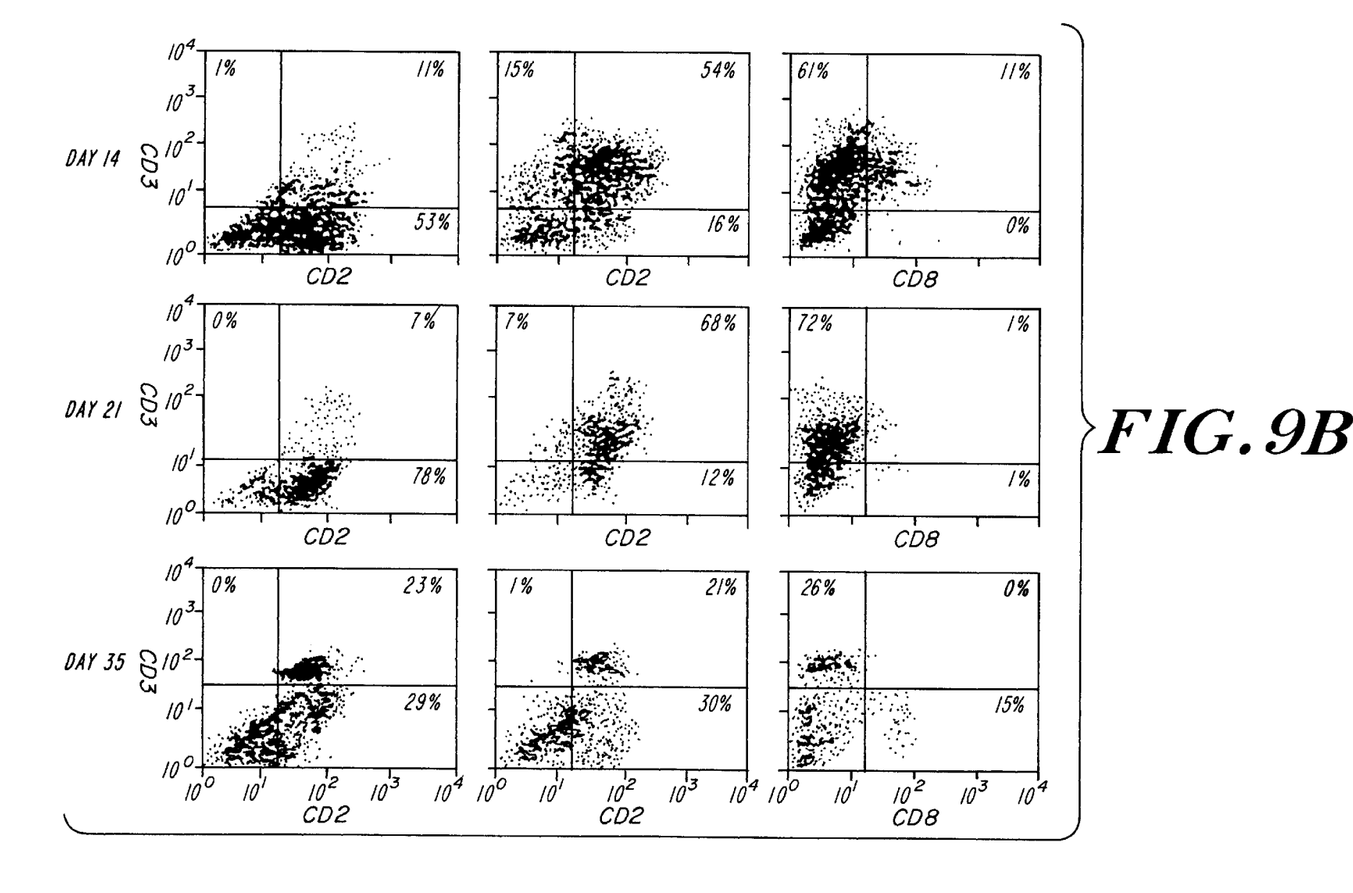

FIG. 9 shows other typical flow cytometric analyses of CD34+, CD2− bone marrow cells cultured in the described system for the internal indicated.

PMA/PHA-stimulated IL-2 production by cultured cells

In order to confirm the presence of relatively mature T cells in the harvested cells, aliquots of $10^5$ cells in 200 µl IMDM/20% FCS were cultured with and without the addition of phytohemagglutinin (PHA), 3 µg/ml, and phorbol myristic acid (PMA), 50 ng/ml (both Sigma). The CD2+ fraction of bone marrow MNC, separated as described above, was used as a positive control. The culture supernatants were harvested after 48 h and stored at −20° C. before assaying the interleukin-2 (IL-2) concentration by ELISA (R & D Systems). Low, but detectable, levels of IL-2 were observed in the culture supernatants.

Reverse-transcription-coupled polymerase chain reaction (RT-PCR) for RAG-2 and IL-2 gene expression Total RNA was prepared from between $10^3$–$10^4$ sorted or cultured cells by guanidinium isothiocyanate extraction and pelleted by ultracentrifugation through cesium chloride. cDNA was prepared by reverse transcription using random primers and Moloney reverse transcriptase (Gibco-BRL), and was amplified using primers specific for a 415 basepair (bp) region of the human RAG-2 gene, which is expressed transiently only by cells undergoing lymphocyte differentiation. PCR products were analyzed by 2% agarose gel electrophoresis and photographed under UV light after ethidium bromide staining (see FIG. 4). Specificity was confirmed by Southern blot hybridization with a $^{32}$P-labelled 32 base probe, followed by autoradiography.

Example 2

Infection of In Vitro-Produced T-Cells With HIV-2$_{IIIB}$

Cell-free HIV-1$_{IIIB}$ or mock virus preparations were added to in vitro T-cell cultures to determine susceptibility to HIV-1 infection. Supernatants were collected at intervals of 3–4 days and HIV p24 antigen levels were measured by ELISA.

EQUIVALENTS

It should be understood that the preceding is merely a detailed description of certain preferred embodiments of the present invention. It therefore should be apparent to those skilled in the art that various modifications and equivalents can be made without departing from the spirit or scope of the invention.

What is claimed is:

1. A method of producing a population of human T-cells having a specific characteristic antigenic profile in vitro comprising:

providing a population of human precursor cells expressing CD34; and culturing said precursor cells in the presence of interleukin-12 (IL-12) at a concentration of about 10 ng/ml and flk2/flt3 ligand at a concentration pf about 100 ng/ml to generate said population of human T-cells having the following characteristics: approximately 17–74% of the T-cells express CD2, approximately 1.5–34% of the T-cells express CD3, approximately 16–61% of the T-cells express CD4 and approximately 0–15% of the T-cells express CD8 and recovering said population of human T-cells having said specific characteristic antigenic profile.

2. The method of claim 1 wherein said population of human precursor cells expressing CD34 is prepared from bone marrow cells, fetal liver cells, umbilical cord blood cells or peripheral blood cells.

3. The method of claim 1, further comprising the step of providing a confluent monolayer of thymic stroma wherein said confluent monolayer of thymic stroma is placed in contact with said population of precursor cells expressing CD34.

4. The method of claim 3, wherein the step of providing a confluent monolayer of thymic stroma comprises:

providing human fetal thymic tissue;

preparing said confluent monolayer from cells from said human fetal thymic tissue.

* * * * *

UNITED STATES PATENT AND TRADEMARK OFFICE
CERTIFICATE OF CORRECTION

PATENT NO. : 6,004,812
DATED : December 21, 1999
INVENTOR(S) : David T. Scadden and Andrew Freedman It is certified that error appears in the above-identified patent and that said Letters Patent is hereby corrected as shown below:

Column 2, line 34, replace "immunodeficiency." with --immunodeficiency--.

Column 3, line 65, replace "cell sorter SACS)" with --cell sorter (FACS)--.

Column 11, line 9, replace "pf" with --of--.

Column 11, line 15, after "CD8" add --,--.

Signed and Sealed this

Tenth Day of April, 2001

Attest:

NICHOLAS P. GODICI

Attesting Officer      Acting Director of the United States Patent and Trademark Office